US00PP33698P2

(12) United States Plant Patent
Fouillet

(10) Patent No.: US PP33,698 P2
(45) Date of Patent: Nov. 30, 2021

(54) APPLE TREE NAMED 'S01A'

(50) Latin Name: *Malus domestica*
Varietal Denomination: S01A

(71) Applicant: IFO S.A.R.L., Seiches sur le Loir (FR)

(72) Inventor: Valérie Fouillet, Saint Sylvain d'Anjou (FR)

(73) Assignee: IFO S.A.R.L., Seiches sur le Loir (FR)

( * ) Notice: Subject to any disclaimer, the term of this patent is extended or adjusted under 35 U.S.C. 154(b) by 0 days.

(21) Appl. No.: 17/300,408

(22) Filed: Jun. 16, 2021

(30) Foreign Application Priority Data

Aug. 27, 2020 (FR) ..... 21063

(51) Int. Cl.
*A01H 5/08* (2018.01)

(52) U.S. Cl.
USPC ..... Plt./172

(58) Field of Classification Search
USPC ..... Plt./172
See application file for complete search history.

*Primary Examiner* — Susan McCormick Ewoldt
(74) *Attorney, Agent, or Firm* — Michelle Bos Legal LLC

(57) ABSTRACT

'S01A' is a new apple tree selected for its small yellow fruit, which is well-suited for fresh consumption.

8 Drawing Sheets

Latin name: *Malus domestica.*
Variety denomination: 'S01A'.

BACKGROUND OF THE VARIETY:

'S01A' is a new and distinct apple tree (*Malus domestica*) obtained from a controlled cross of 'Silken' (female parent, U.S. Plant Pat. No. 10,740) x '8S6923', also known as Aurora Golden Gala™ (male parent, not patented) carried out at Seiches sur le Loir, France in 2006. Seeds obtained from the cross were planted at Seiches sur le Loir, 'S01A' was selected from the resulting seedlings for propagation and further observation. 'S01A' trees were first asexually propagated by grafting at Seiches sur le Loir in 2007, and have since been observed to remain true to type through successive asexually propagated generations.

BRIEF DESCRIPTION OF THE VARIETY

The 'S01A' apple tree (originally identified by breeder's reference "GC3-2") is distinguished by its small yellow fruit, which is well-suited for fresh consumption. Comparisons of 'S01A' to its parents and to similar variety 'Golden Parsi' (U.S. Plant Pat. No. 22,859) are shown in Tables 1, 2 and 3 below.

TABLE 1

Comparison of 'S01A' to Female Parent 'Silken'

| Characteristic | 'S01A' | 'Silken' |
|---|---|---|
| Size of fully open flower | Smaller, 33 × mm | Larger, 56 mm |
| Leaf size | Smaller, 73 mm × 47 mm | Larger, 86 mm × 58 mm |
| Fruit weight | Smaller, 54 g | Larger, 180 g to 220 g |
| Juiciness | Medium juicy | Very juicy |
| Fruit overcolor | Light brown 173C | Pink 46A |

TABLE 2

Comparison of 'S01A' to Male Parent '8S6923'

| Characteristic | 'S01A' | '8S6923' |
|---|---|---|
| Fruit weight | Smaller, 54 g | Larger, 221 g |
| Date of full bloom (2018) | Earlier, Apr. 9 | Later, Apr. 19 |
| Length of fruit stalk | 12 mm | 30 mm to 40 mm |
| Fruit shape | Globose | Cylindrical |
| Fruit firmness | Weak to medium | Medium to high |

TABLE 3

Comparison of 'S01A' to Similar Variety 'Golden Parsi'

| Characteristic | 'S01A' | 'Golden Parsi' |
|---|---|---|
| Harvest maturity | Earlier | Later, 1 month after 'S01A' |
| Fruit size | Smaller, 54 g | Larger, 240 g |
| Date of full bloom (2018) | Earlier, Apr. 9 | Later, Apr. 23 |
| Flowers per cluster | 4 to 5 | 5 to 7 |
| One-year-old shoot color | Medium brown 165A | Grey-brown N199B |

BRIEF DESCRIPTION OF THE PHOTOGRAPHS

The accompanying photographs were obtained at Seiches sur le Loir, France. The trees shown were planted in 2013. Photos of the tree, shoots and leaves were taken in 2016, the flower bud photo was taken in 2017 and the fruit photos were taken in 2020.

DETAILED BOTANICAL DESCRIPTION OF THE VARIETY

Figure 1:
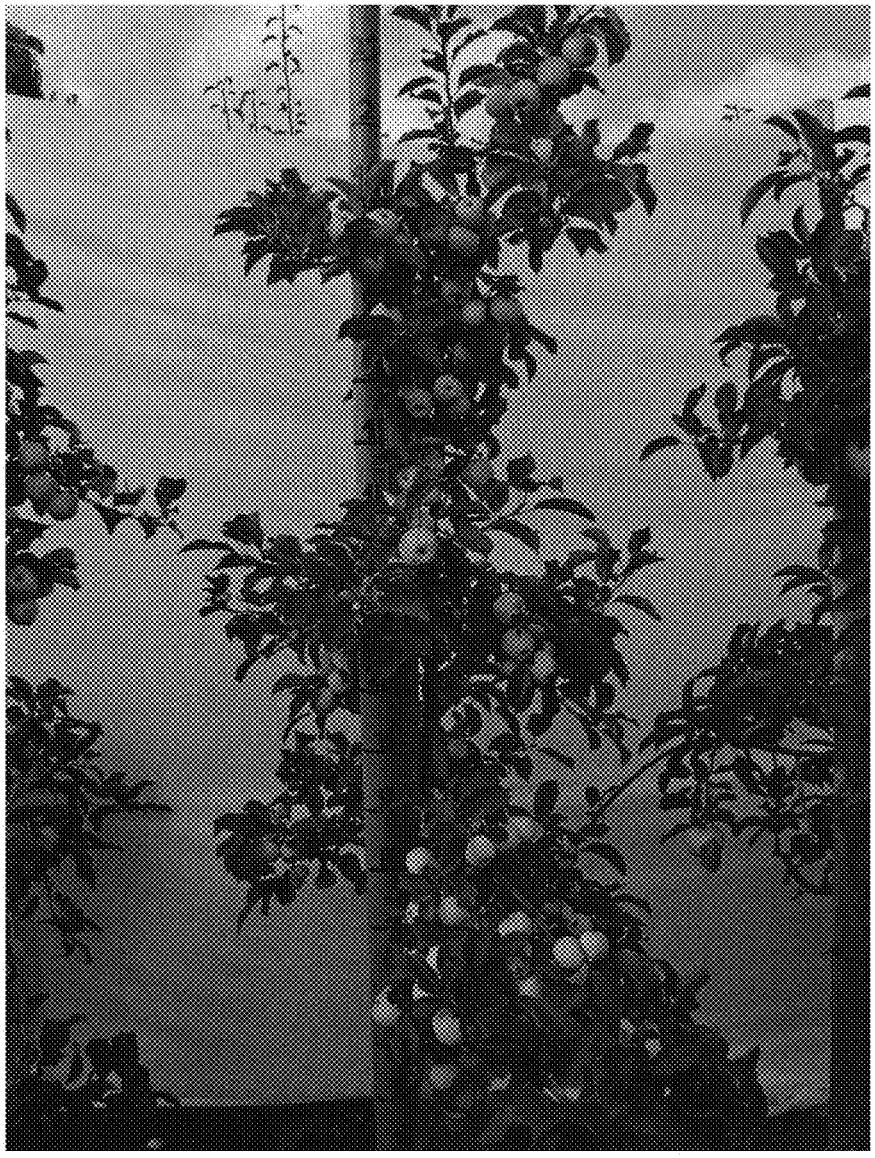
FIG. 1 is a photograph of an 'S01A' apple tree with leaves and fruit.
Figure 2:
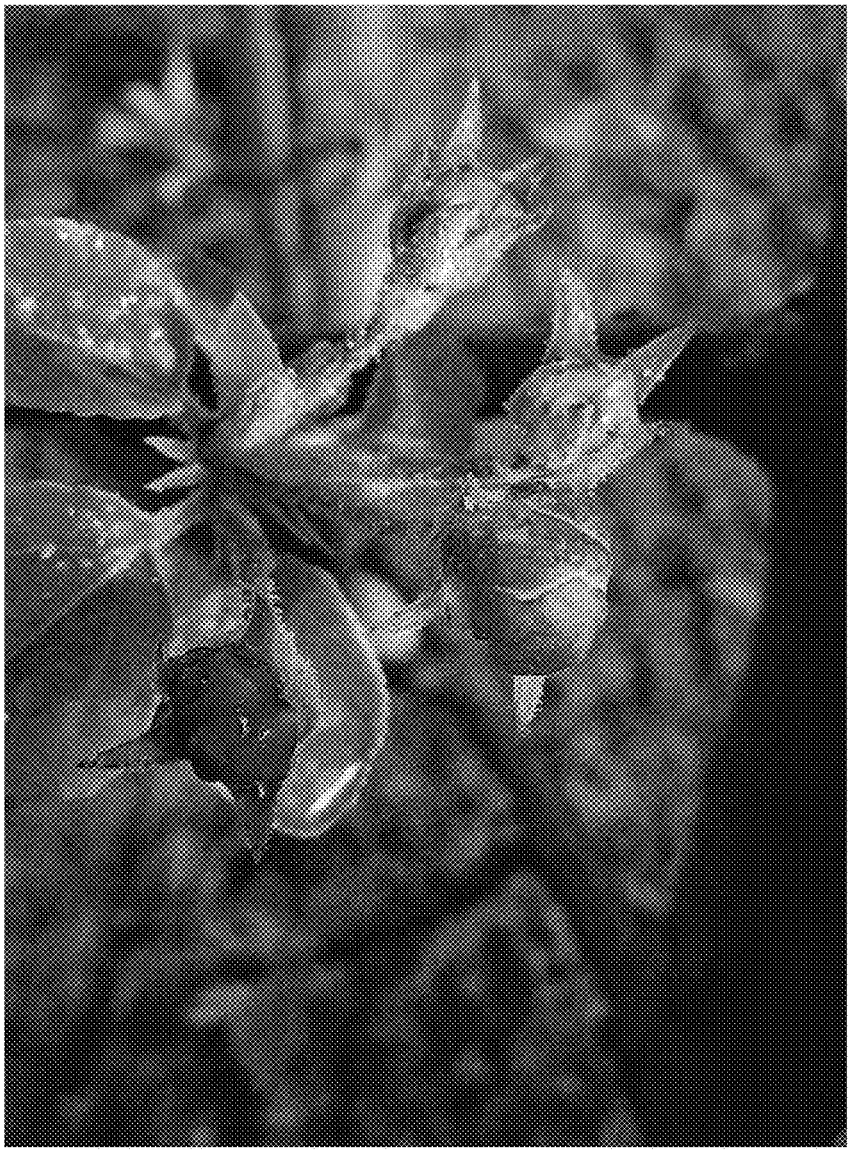
FIG. 2 is a photograph of a flower bud on an 'S01A' apple tree.
Figure 3:
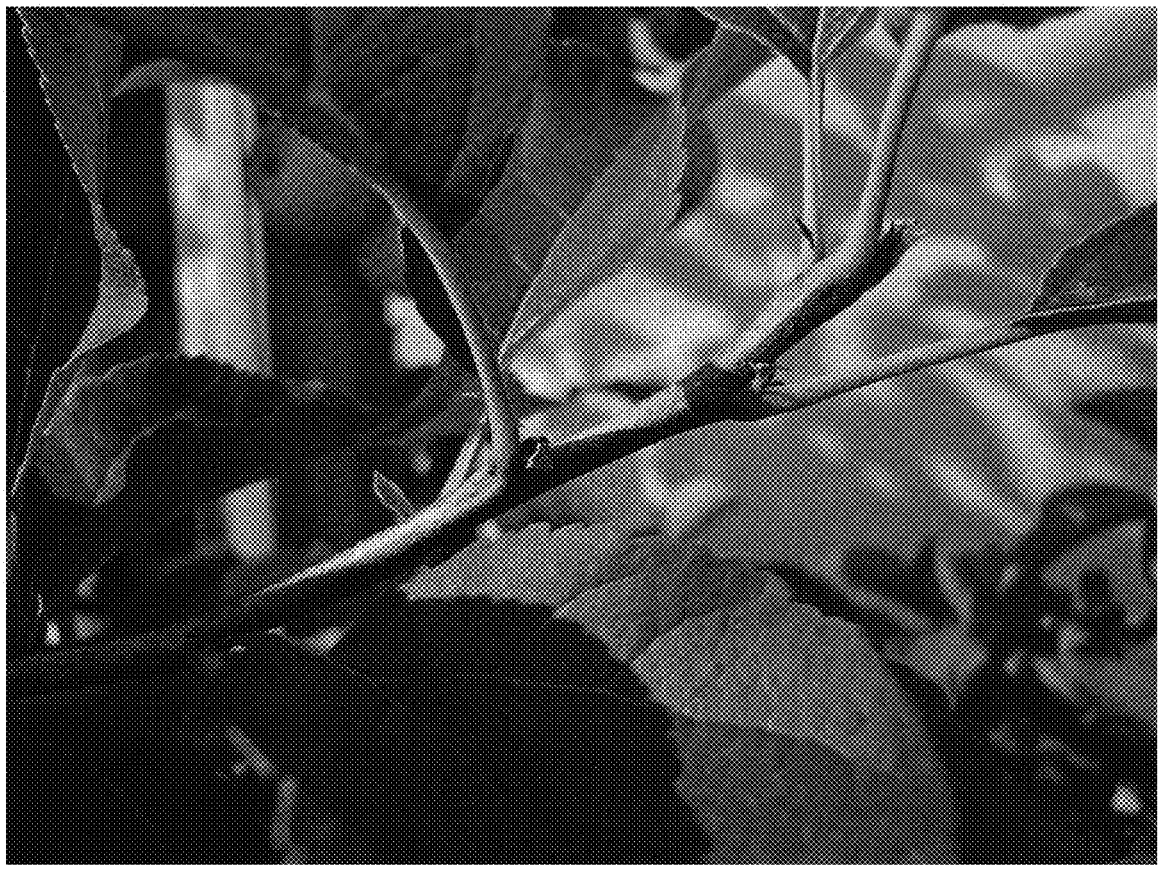
FIG. 3 is a photograph of a one-year-old shoot of an 'S01A' apple tree.
Figure 4:
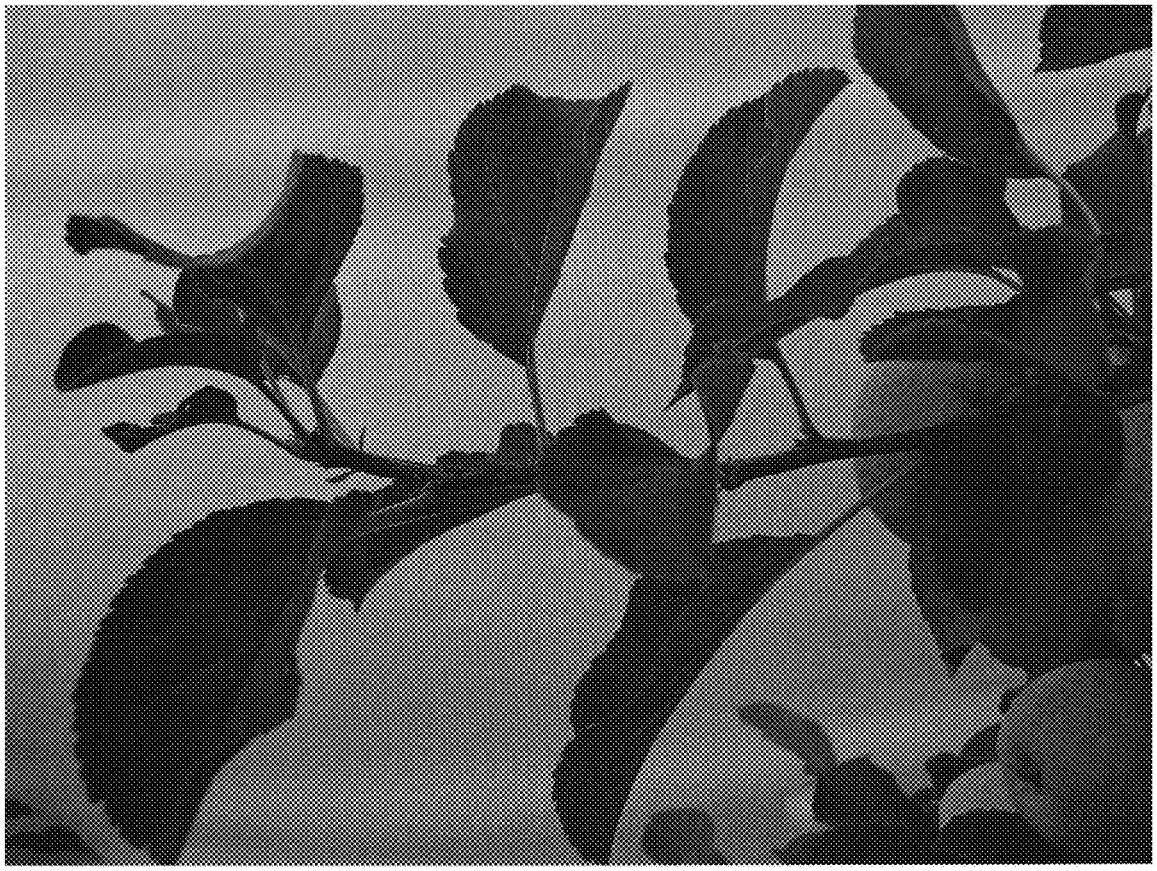
FIG. 4 is a photograph of leaves of an 'S01A' apple tree.
Figure 5:
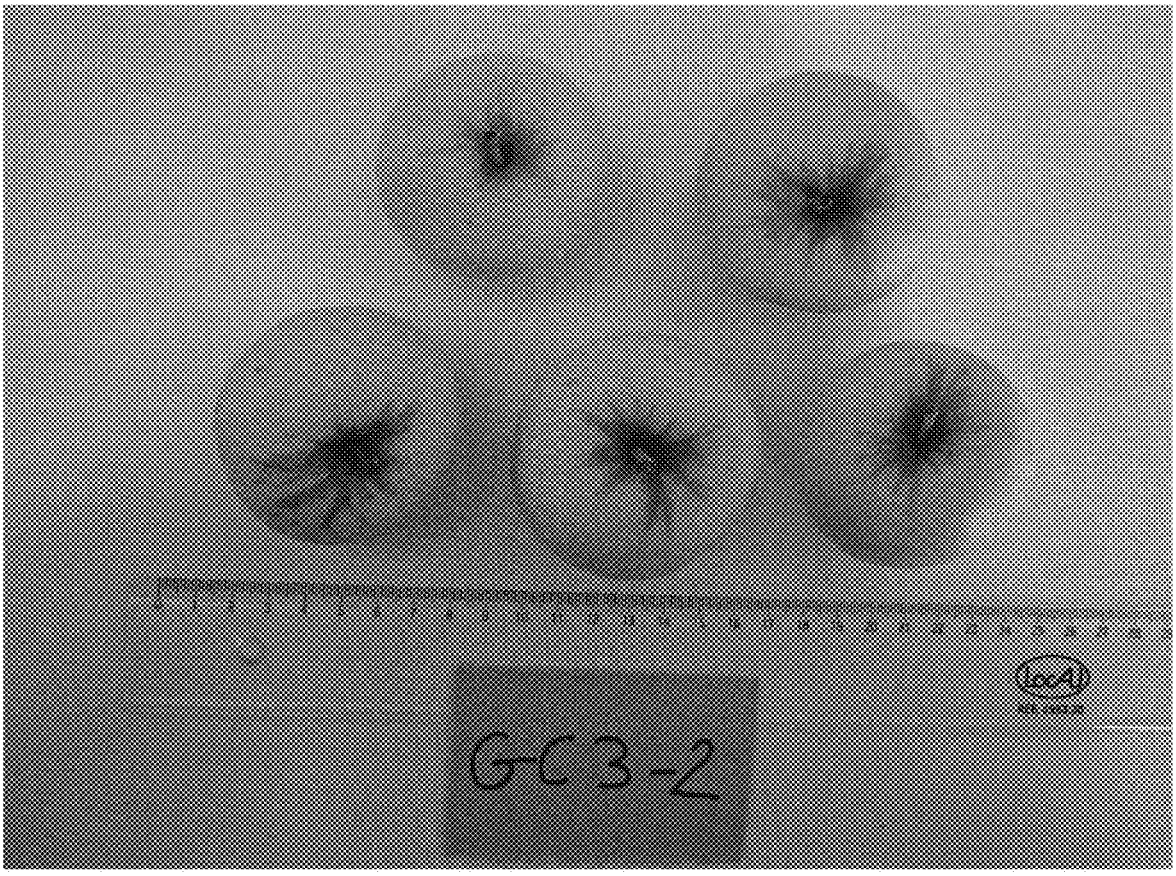
FIG. 5 is a photograph of whole fruit from an 'S01A' apple tree.
Figure 6:
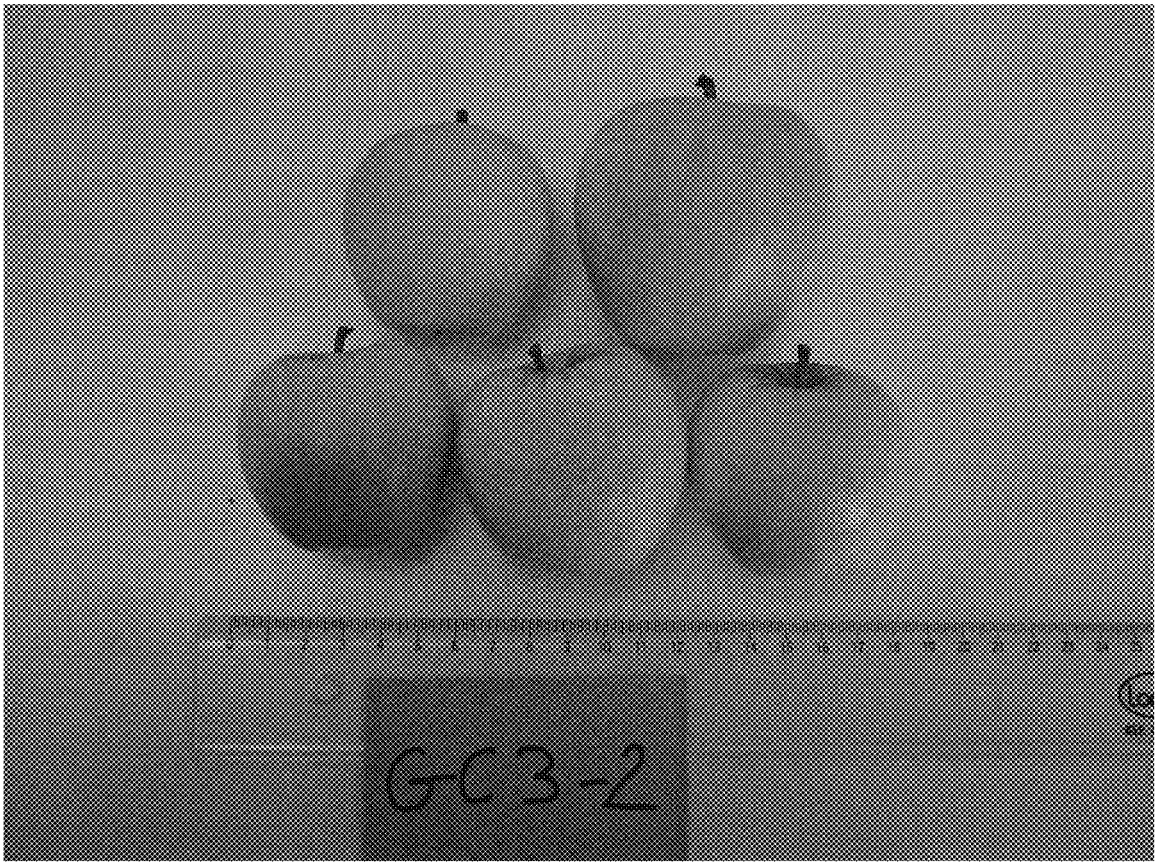
FIG. 6 is a photograph of whole fruit from an 'S01A' apple tree.
Figure 7:
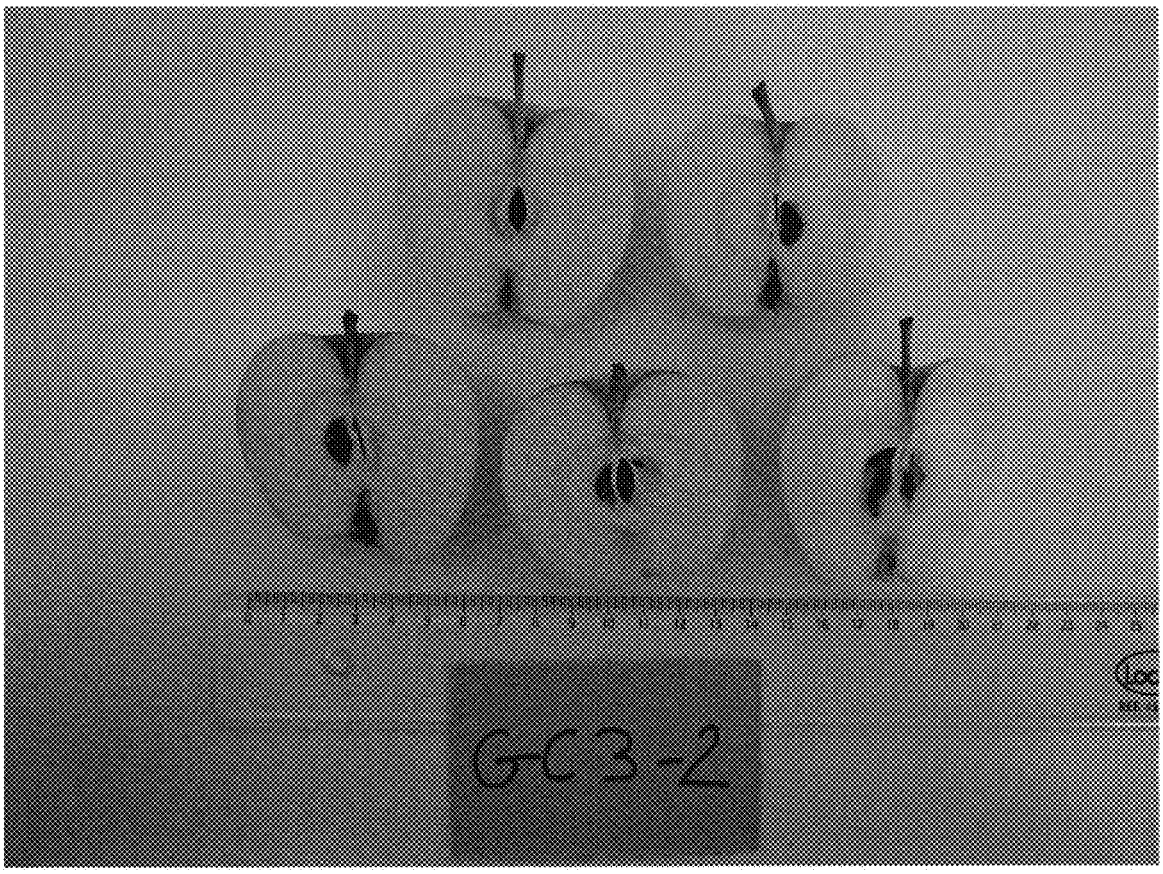
FIG. 7 is a photograph of sectioned fruit from an 'S01A' apple tree.
Figure 8:
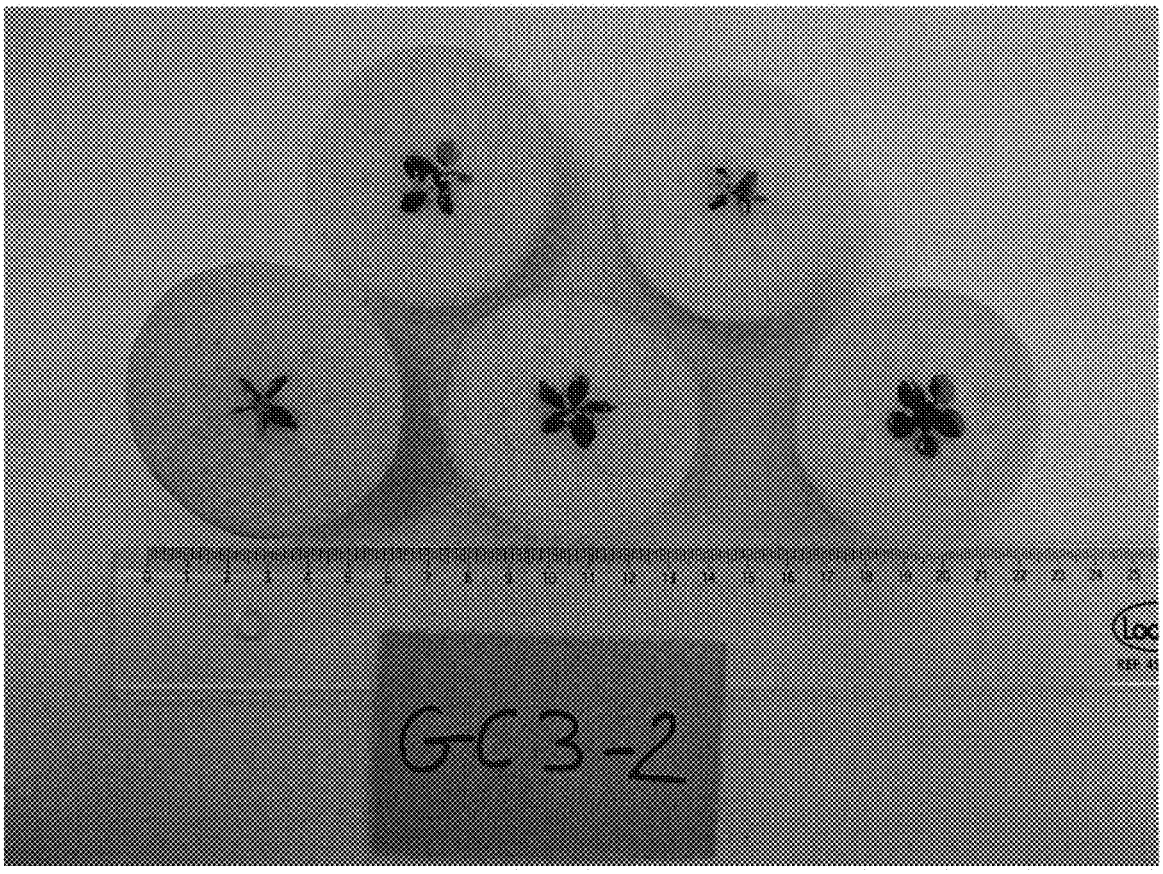
FIG. 8 is a photograph of sectioned fruit from an 'S01A' apple tree.

The following detailed botanical description was recorded at Seiches sur le Loir, France from 2016 to 2018. The described trees were trees planted in 2013 on Pajam®2 'Cepiland' (U.S. Plant Pat No. 7,715) rootstock. All colors are described according to The RHS Mini Colour Chart (Royal Horticultural Society, 2005). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor.*—Weak.
- *Type.*—Ramified.
- *Habit.*—Spreading.
- *Bearing.*—On shoots.
- *Spread of mature tree.*—1.5 meters.
- *Height.*—2.3 m.
- *Trunk diameter* (*at* 30 *cm above the graft*).—31 mm.
- *Bark texture.*—Smooth.
- *Bark color.*—Grey N200C.
- *Lenticel length.*—3 mm.
- *Lenticel width.*—1.0 mm.
- *Lenticel height.*—0.4 mm.
- *Lenticel shape.*—Oblong.
- *Lenticel color.*—Yellow orange 22A.

Branch (fruiting branches located at around 1 m above the graft union):
- *Length.*—85 cm.
- *Diameter.*—17 mm.
- *Crotch angle.*—90°.
- *Bark color.*—Grey N200C.
- *Lenticel length.*—1.8 mm.
- *Lenticel width.*—1.2 mm.
- *Lenticel height.*—0.3 mm.
- *Lenticel shape.*—Round to oblong.
- *Lenticel color.*—Light yellow orange 19B.
- *Lenticel density.*—About 3 per $cm^2$.

One year old shoot:
- *Length.*—26 cm.
- *Diameter.*—4 mm to 6 mm.
- *Color.*—Medium brown 165A.
- *Pubescence.*—Medium.
- *Internode length.*—25 mm.
- *Lenticel length.*—1.3 mm.
- *Lenticel width.*—0.5 mm.
- *Lenticel height.*—0.2 mm.
- *Lenticel shape.*—Round to oblong.
- *Lenticel color.*—Light yellow orange 18C.

Flower buds:
- *Quantity per spur.*—4 to 5.
- *Bud shape.*—Round to conical.
- *Apex shape.*—Rounded.
- *Length.*—11 mm.
- *Diameter.*—9 mm.
- *Color.*—Purple 58A.

Flowers:
- *Diameter of fully open flower.*—33 mm.
- *Depth of fully open flower.*—17 mm.
- *Relative position of petal margin.*—Overlapping.
- *Number per cluster.*—4 to 5.
- *Date of first bloom* (2018).—April 6.
- *Date of full bloom* (2018).—April 9.
- *Pollination requirement.*—Pollenizer required.
- *Fragrance.*—Weak, fresh.

Petals:
- *Number per flower.*—5.
- *Petal shape.*—Elliptical.
- *Length.*—24 mm.
- *Width.*—14 mm.
- *Apex shape.*—Obtuse.
- *Base shape.*—Acute.
- *Margin.*—Entire.
- *Color of upper surface.*—Light blue violet 76B with white N155B.
- *Color of lower surface.*—Blue violet N82D with white N155B.

Pistils:
- *Quantity.*—5.
- *Length.*—12 mm.
- *Color.*—Light green 145A.

Stigma:
- *Length.*—1 mm.
- *Color.*—Light green 145A.

Style:
- *Length.*—8 mm.
- *Color.*—Light green 145C.

Ovary:
- *Length.*—3 mm.
- *Diameter.*—1.3 mm.
- *Color.*—Brown green 146C.

Stamens:
- *Quantity.*—20.
- *Anther length.*—2 mm.
- *Anther diameter.*—1 mm.
- *Color of anther.*—Light yellow 8C.
- *Pollen presence.*—Present in moderate quantity.
- *Pollen color.*—Light yellow 8C.

Pedicel:
- *Length.*—20 mm.
- *Diameter.*—1.5 mm.
- *Color.*—Brown green 146C.

Sepals:
- *Quantity.*—5.
- *Color of upper surface.*—Light green 145B.
- *Color of lower surface.*—Light green 145A.
- *Length.*—6 mm.
- *Width.*—3 mm.
- *Sepal shape.*—Pointed.
- *Apex shape.*—Acute.
- *Margin* (*smooth, serrated, etc.*).—Entire.

Leaves:
- *Shape.*—Elliptical.
- *Length.*—73 mm.
- *Width.*—47 mm.
- *Length to width ratio.*—1.55.
- *Leaf margin.*—Biserrate.
- *Apex.*—Acuminate.

*Base shape.*—Cuneate.
*Leaf color-upper surface.*—Brown green 137A.
*Leaf color-lower surface.*—Brown green 137C.
*Attitude in relation to shoot.*—Upward.

Petiole:
*Length.*—23 mm.
*Diameter.*—1.5 mm.
*Color.*—Light green 145C.

Fruit:
*Quantity per cluster.*—5.
*Diameter.*—49 mm.
*Height.*—42 mm.
*Ratio of height to width.*—0.86.
*Weight.*—54 g.
*General shape in profile.*—Globose.
*Position of maximum diameter.*—Upper middle.
*Ribbing.*—Weak.
*Crowning at calyx end.*—Moderate.
*Bloom of skin.*—Weak.
*Greasiness of skin.*—Weak.
*Background color of skin.*—Light yellow 8C.
*Over color of skin.*—Light brown 173C.
*Amount of over color.*—Usually about 30%.
*Intensity of over color.*—Medium.
*Pattern of over color.*—Solid flush.
*Amount of russet around stalk cavity.*—Medium.
*Amount of russet on cheeks.*—Absent or weak.
*Area of russet around eye basin.*—Absent or weak.
*Stalk length.*—12 mm.
*Stalk diameter.*—2 mm.
*Stalk color.*—Light green 145A with medium brown 165A.
*Depth of stalk cavity.*—7.5 mm.
*Width of stalk cavity.*—19 mm.
*Depth of eye basin.*—3 mm.
*Width of eye basin.*—20 mm.
*Aperture of eye.*—Closed.
*Length of sepal.*—6 mm.
*Firmness of flesh.*—Weak to medium.
*Flavor.*—Acid level weak; sugar medium to high (14° Brix).
*Aroma.*—Medium.
*Juiciness.*—Medium juicy.
*Flesh color.*—Light yellow 4D.

Seeds:
*Quantity per fruit.*—7.
*Length.*—5 mm.
*Shape.*—Oval-oblong.
*Color.*—Dark brown 200B.

Harvest:
*Harvest date.*—Early, similar to 'Gala'; Aug. 21, 2018.
*Number of picks.*—2.
*Productivity.*—200 fruits per tree in full production.

Storageability: Weak to medium.

Market use: Fresh consumption.

The invention claimed is:

1. A new and distinct apple tree substantially as described and illustrated herein.

* * * * *